US012121751B2

(12) United States Patent
Meir et al.

(10) Patent No.: US 12,121,751 B2
(45) Date of Patent: *Oct. 22, 2024

(54) PATIENT MONITOR

(71) Applicant: VISION RT LIMITED, London (GB)

(72) Inventors: Ivan Meir, London (GB); Kathryn Cooper, London (GB); Norman Smith, London (GB); Gideon Hale, London (GB); Martin Allen, London (GB)

(73) Assignee: VISION RT LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/122,957

(22) Filed: Mar. 17, 2023

(65) Prior Publication Data

US 2023/0293908 A1 Sep. 21, 2023

Related U.S. Application Data

(63) Continuation of application No. 17/087,812, filed on Nov. 3, 2020, now Pat. No. 11,628,313, which is a
(Continued)

(30) Foreign Application Priority Data

Oct. 12, 2012 (GB) ..................... 1218307

(51) Int. Cl.
*A61N 5/10* (2006.01)
*A61B 90/00* (2016.01)
(Continued)

(52) U.S. Cl.
CPC ............ *A61N 5/1049* (2013.01); *A61B 90/39* (2016.02); *A61N 5/1069* (2013.01);
(Continued)

(58) Field of Classification Search
None
See application file for complete search history.

(56) References Cited

U.S. PATENT DOCUMENTS 6,535,574 B1 3/2003 Collins et al.
7,014,361 B1 3/2006 Ein-Gal
(Continued)

FOREIGN PATENT DOCUMENTS

CN 1476813 A 2/2004
EP 1640922 A2 3/2006
(Continued)

OTHER PUBLICATIONS

Aug. 1, 2016 Office Action issued in Chinese Patent Application No. 201380052008.6 (with English translation).
(Continued)

*Primary Examiner* — Thaddeus B Cox
(74) *Attorney, Agent, or Firm* — Birch, Stewart, Kolasch & Birch, LLP (57) ABSTRACT

Images obtained by a camera system (10) arranged to obtain images of a patient (20) undergoing radio-therapy are processed by a modeling unit (56,58) which generates a model of the surface of a patient (20) being monitored. Additionally the patient monitoring system processes image data not utilized to generate a model of the surface of a patient being monitored to determine further information concerning the treatment of the patient (20). Such additional data can comprise data identifying the relative location of the patient and a treatment apparatus (16). This can be facilitated by providing a number or retro-reflective markers (30-40) on a treatment apparatus (16) and a mechanical couch (18) used to position the patient (20) relative to the treatment appara-
(Continued)

tus (16) and monitoring the presence and location of the markers in the portions of the images obtained by the stereoscopic camera (10).

11 Claims, 6 Drawing Sheets

Related U.S. Application Data continuation of application No. 16/230,739, filed on Dec. 21, 2018, now Pat. No. 10,926,109, which is a continuation of application No. 14/424,376, filed as application No. PCT/GB2013/052650 on Oct. 11, 2013, now Pat. No. 10,183,177.

(51) Int. Cl.
 *G06T 7/285* (2017.01)
 *G06T 7/73* (2017.01)
 *H04N 13/204* (2018.01)

(52) U.S. Cl.
 CPC ............ *A61N 5/1081* (2013.01); *G06T 7/285* (2017.01); *G06T 7/73* (2017.01); *H04N 13/204* (2018.05); *A61B 2090/3904* (2016.02); *A61B 2090/3937* (2016.02); *A61B 2576/00* (2013.01); *A61N 2005/1059* (2013.01); *A61N 2005/1074* (2013.01); *G06T 2207/10021* (2013.01); *G06T 2207/30196* (2013.01); *G06T 2207/30204* (2013.01)

(56) References Cited

U.S. PATENT DOCUMENTS

| | | |
|---|---|---|
| 7,348,974 B2 | 3/2008 | Smith et al. |
| 7,889,906 B2 | 2/2011 | Smith et al. |
| 2003/0123609 A1 | 7/2003 | Manske |
| 2004/0122311 A1 | 6/2004 | Cosman |
| 2005/0054910 A1 | 3/2005 | Tremblay et al. |
| 2005/0228255 A1 | 10/2005 | Saracen et al. |
| 2005/0234327 A1 | 10/2005 | Saracen et al. |
| 2005/0281374 A1 | 12/2005 | Cheng et al. |
| 2006/0122502 A1 | 6/2006 | Scherch et al. |
| 2009/0003975 A1 | 1/2009 | Kuduvalli et al. |
| 2009/0018711 A1 | 1/2009 | Ueda et al. |
| 2009/0052760 A1 | 2/2009 | Smith et al. |
| 2009/0196401 A1 | 8/2009 | Awan et al. |
| 2011/0228907 A1 | 9/2011 | Gagnon et al. |
| 2011/0249088 A1 | 10/2011 | Hannibal et al. |
| 2013/0142310 A1 | 6/2013 | Fahimian et al. |
| 2013/0184005 A1 | 7/2013 | Hieronimi |

FOREIGN PATENT DOCUMENTS

| | | |
|---|---|---|
| GB | 2390792 B | 8/2005 |
| JP | 2011110335 A | 6/2011 |
| WO | WO 9927839 A2 | 6/1999 |
| WO | WO 2012119649 A1 | 9/2012 |

OTHER PUBLICATIONS

Jan. 16, 2013 Combined Search and Examination Report issued in GB Patent Application No. 1218307.5.
Jun. 6, 2016 Examination report received issued in European Patent Application No. 13777329.7.
Second Office Action issued Feb. 7, 2017 to Chinese patent application No. 201380052008.6.

PATIENT MONITOR

This application is a Continuation of co-pending application Ser. No. 17/087,812 filed on Nov. 3, 2020 (now U.S. Pat. No. 11,628,313 issued Apr. 18, 2023), which is a Continuation of application Ser. No. 16/230,739 filed on Dec. 21, 2018 (now U.S. Pat. No. 10,926,109 issued Feb. 23, 2021), which is a Continuation of application Ser. No. 14/424,376 filed on Feb. 26, 2015 (now U.S. Pat. No. 10,183,177 issued on Jan. 22, 2019), which is a National Phase of PCT International Application No. PCT/GB2013/052650 filed on Oct. 11, 2013, which claims priority under 35 U.S.C. § 119(a) to Patent Application No. 1218307.5 filed in the United Kingdom on Oct. 12, 2012. All of the above applications are hereby expressly incorporated by reference into the present application.

The present invention relates to patient monitoring. More particularly, embodiments of the present invention relate to monitoring the positioning of patients and also to enable the movement of patients to be detected. The invention is particularly suitable for use with radiotherapy devices and the like where accurate positioning and the detection of patient movement is important for successful treatment.

Radiotherapy consists of projecting onto a predetermined region of a patient's body, a radiation beam so as to destroy or eliminate tumours existing therein. Such treatment is usually carried out periodically and repeatedly. At each medical intervention, the radiation source must be positioned with respect to the patient in order to irradiate the selected region with the highest possible accuracy to avoid radiating adjacent tissue on which radiation beams would be harmful.

When applying radiation to a patient, the gating of treatment apparatus should be matched with the breathing cycle so that radiation is focused on the location of a tumour and collateral damage to other tissues is minimized. If movement of a patient is detected the treatment should be halted to avoid irradiating areas of a patient other than a tumour location.

For this reason a number of monitoring systems for assisting the positioning of patients during radiotherapy have therefore been proposed such as those described in Vision RT's earlier patents and patent applications U.S. Pat. Nos. 7,348,974, 7,889,906 and US2009-018711 all of which are hereby incorporated by reference.

In the systems described in Vision RT's patent applications, stereoscopic images of a patient are obtained and processed to generate data identifying 30 positions of a large number of points corresponding to points on the surface of an imaged patient. Such data can be compared with data generated on a previous occasion and used to position a patient in a consistent manner or provide a warning when a patient moves out of position. Typically such a comparison involves undertaking Procrustes analysis to determine a transformation which minimizes the differences in position between points on the surface of a patient identified by data generated based on live images and points on the surface of a patient identified by data generated on a previous occasion.

Treatment plans for the application of radiotherapy are becoming increasingly complex with treatment apparatus having multiple or floating iso-centres. Such increasing complexity brings with it increasing possibilities of mistreatment. There is therefore a need for a monitoring system which can detect when errors occur and halt treatment when such errors are detected.

SUMMARY OF INVENTION

In accordance with one aspect of the present invention there is provided a patient monitoring system for monitoring a patient undergoing radiotherapy comprising: a stereoscopic camera system operable to obtain stereoscopic images of a patient undergoing radiotherapy; a modeling unit operable to process stereoscopic images of a patient and generate a model of the surface of a patient being monitored on the basis of the appearance of the patient corresponding to part of the stereoscopic images obtained by the stereoscopic camera system; wherein the patient monitoring system is arranged to process image data corresponding to portions of the stereoscopic images which are not utilized to generate a model of the surface of a patient being monitored to determine further information concerning the treatment of the patient.

The patient monitoring system may comprise an apparatus position determination module operable to process stereoscopic images obtained by the stereoscopic camera system and utilize portions of the stereoscopic images which are not utilized to generate a model of the surface of a patient being monitored to determine the relative positioning of a treatment apparatus relative to a patient.

The patient monitoring system may be incorporated in a treatment system which includes a treatment apparatus for treating a patient; and a mechanical couch for positioning a patient relative to the treatment apparatus. In such a system a plurality of markers may be attached to the surface of the treatment apparatus and the patient monitoring system may be arranged to process images of the markers contained in portions of the stereoscopic images which are not utilized to generate a model of the surface of a patient to determine the relative positioning of a treatment apparatus relative to a patient.

The treatment apparatus may comprise a gantry operable to rotate about an axis relative to a main body of the apparatus. In such a system, at least some of the markers may be provided on the surface of the treatment apparatus arranged such that the apparatus position determination module is operable to determine the relative rotation of the gantry about the axis on the basis of the positions of the markers in the portions of the stereoscopic images which are not utilized to generate a model of the surface of a patient.

In some systems the treatment apparatus may comprise a rotatable collimator provided at the end of the gantry remote from the main body of the apparatus where the rotatable collimator is operable to rotate about an axis perpendicular to the axial extent of the gantry. In such a system, at least some of the markers may be provided on the surface of the treatment apparatus arranged such that the apparatus position determination module is operable to determine the relative rotation of the collimator on the basis of the positions of the markers in the portions of the stereoscopic images which are not utilized to generate a model of the surface of a patient. In some embodiments this may be achieved by the markers being provided on the surface of the treatment apparatus in a number of groups and the apparatus position determination module may be operable to determine the extent of rotation based on the presence of one or more groups of markers in the portions of the stereoscopic images which are not utilized to generate a model of the surface of a patient.

In some embodiments one or more markers may be attached to the mechanical couch and the apparatus position determination module may be operable to determine the relative positions of the mechanical couch relative to the position of the treatment apparatus on the basis of the position of the one or more markers attached to the mechanical couch in the portions of the stereoscopic images which are not utilized to generate a model of the surface of a patient.

Where markers are attached to the treatment apparatus or the mechanical couch, the markers may comprise retro-reflective markers and the stereoscopic camera system may include a light source for illuminating the markers. In such an embodiment the apparatus position determination module may be arranged to identify portions of the stereoscopic images which are not utilized to generate a model of the surface of the patient and which correspond to the markers by performing a thresholding operation.

In some embodiments, the markers utilized may comprise spherical markers and the apparatus position determination module may be arranged to identify portions of the stereoscopic images which are not utilized to generate a model of the surface of the patient and which correspond to the markers by identifying circular representations of the markers in the images.

The stereoscopic camera system may be operable to obtain a sequence of images of a patient undergoing radiotherapy lying on the mechanical couch. In such a system the apparatus position determination module may be arranged to utilize the detected positions of the markers in the sequence of images to track the relative positioning of a treatment apparatus relative to a patient.

Having determined the relative positioning of a treatment apparatus relative to a patient the monitoring system may then compare the relative positioning of a treatment apparatus relative to a patient with an expected relative positioning based on a predefined treatment plan and provide a warning or halt treatment if the detected positioning of the treatment apparatus does not match with that expected on the basis of the treatment plan.

In addition to confirming that the positioning of the treatment apparatus and the patient correspond with a treatment plan the system may additionally determine the relative positioning of a treatment apparatus relative to a patient and generate a warning if the treatment apparatus is likely to collide with the patient or the mechanical couch.

In some embodiments the positioning of a patient may be facilitated by the use of a face mask worn by a patient and attached to the mechanical couch. In such embodiments the use of the correct face mask may be determined by providing a face mask having distinctive markings thereon. Subsequently the patient monitoring system may process image data corresponding to portions of the stereoscopic images which are not utilized to generate a model of the surface of a patient to detect the presence of the distinctive markings on a face mask and provide a warning if the markings do not correspond to the expected markings for a patient being treated.

In addition to facilitating the checking and confirmation of the adherence to a defined treatment plan the provision of a treatment apparatus and mechanical couch having markers attached also facilitates the calibration of a stereoscopic camera system. In particular monitoring the location of markers attached to a treatment apparatus enables the plane of rotation of a treatment apparatus to be established and hence establish an appropriate co-ordinate system for modeling the location of the patient relative to the axes of movement of the treatment apparatus. Additionally monitoring the motion of markers on a mechanical couch can enable co-ordinates for a volume of interest for monitoring a patient to be mapped out.

BRIEF DESCRIPTION OF THE DRAWINGS

Embodiments of the present invention will now be described with reference to the accompanying drawings in which.

DETAILED DESCRIPTION

Figure 1:
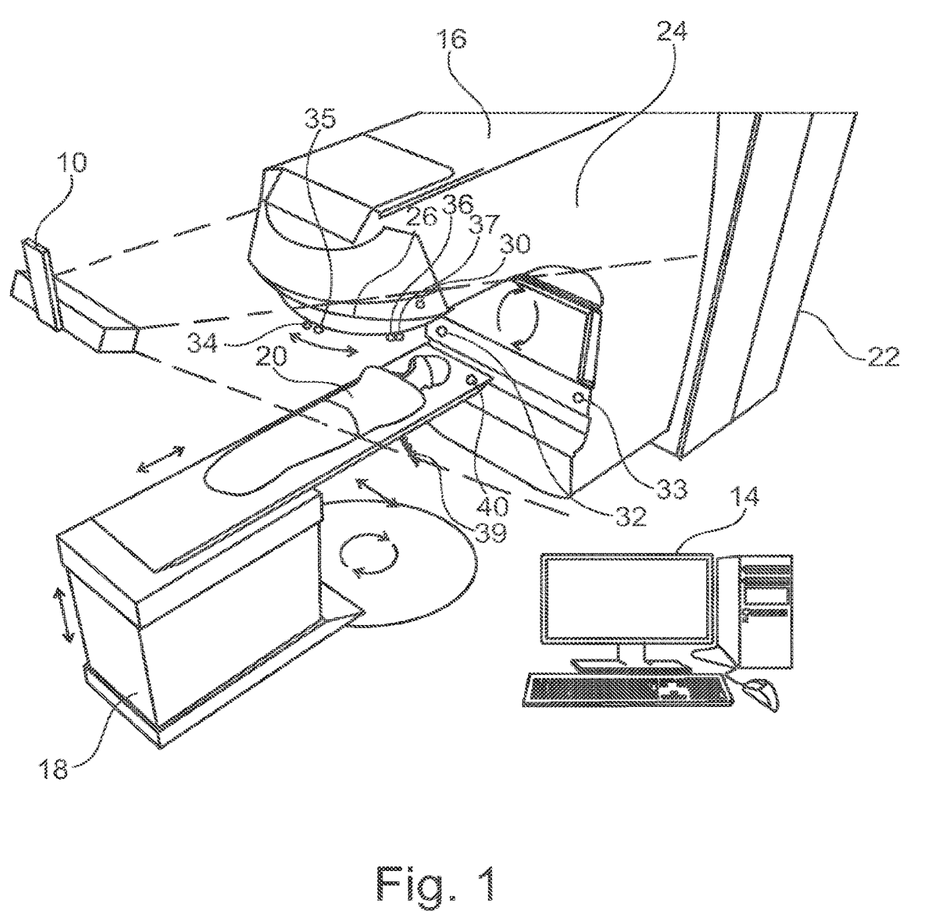
FIG. 1 is a schematic perspective view of a patient monitor in accordance with an embodiment of the present invention.

FIG. 1 is a schematic perspective view of a patient monitor in accordance with an embodiment of the present invention. In accordance with this embodiment, there is provided set of stereoscopic cameras 10 that are connected by wiring (not shown) to a computer 14. The computer 14 is also connected to treatment apparatus 16 such as a linear accelerator for applying radiotherapy. A mechanical couch 18 is provided as part of the treatment apparatus upon which a patient 20 lies during treatment. The treatment apparatus 16 and the mechanical couch 18 are arranged such that, under the control of the computer 14, the relative positions of the mechanical couch 18 and the treatment apparatus 16 may be varied, laterally, vertically, longitudinally and rotationally as is indicated in the figure by the arrows adjacent the couch.

The treatment apparatus 16 comprises a main body 22 from which extends a gantry 24. A collimator 26 is provided at the end of the gantry 24 remote from the main body 22 of the treatment apparatus 16. To vary the angles at which radiation irradiates a patient 20, the gantry 24, under the control of the computer 14, is arranged to rotate about an axis passing through the centre of the main body 22 of the treatment apparatus 16. Additionally the location of irradiation by the treatment apparatus may also be varied by rotating the collimator 26 at the end of the gantry 24.

In use, the stereoscopic cameras 10 obtain video images of a patient 20 lying on the mechanical couch 18. These video images are passed via the wiring to the computer 14. The computer 14 then processes the images of the patient 20 to generate a model of the surface of the patient. This model is compared with a model of the patient generated during earlier treatment sessions. When positioning a patient the difference between a current model surface and a target model surface obtained from an earlier session is identified and the positioning instructions necessary to align the surfaces determined and sent to the mechanical couch 18. Subsequently during treatment any deviation from an initial set up can be identified and if the deviation is greater than a threshold, the computer 14 sends instructions to the treatment apparatus 16 to cause treatment to be halted until a patient 20 can be repositioned.

The applicants have appreciated that the surface of a patient 20 which can be monitored using a set of stereoscopic camera system 10 accounts for only a relatively small portion of the camera system's field of view. Thus for example when monitoring a patient only some or all of a patient's upper torso might be monitored as matching and monitoring such an area is sufficient for the purposes of patient positioning and for detecting patient movement or irregular breathing or the like. Indeed limiting the processing to generate surface data representing only a limited surface area is preferable as limiting the surface area to be monitored reduces the amount of processing necessary to convert image data into a surface model.

Further the applicants have also appreciated that as not all of the image data captured by a stereoscopic camera is required to monitor patient positioning, other portions of the image data can be used for other purposes.

More specifically, as is illustrated in FIG. 1 by dashed lines portions of the treatment apparatus 16 and the mechanical couch 18 are in the field of view of the camera system 10 in addition to portions of the patient 20 which is being monitored. Based on that appreciation, it has become apparent to the applicants that image data captured by the stereoscopic camera system 10 could be utilized to capture real-time information about the positioning of the treatment apparatus 16 and the mechanical couch 18 during treatment. Such data capture could then be utilized to confirm that the treatment apparatus 16 and the mechanical couch 18 were being positioned relative to the patient 20 and hence causing the patient 20 to be irradiated with radiation in accordance with a programmed irradiation program.

As will be described in greater detail, the monitoring of the relative positions of the treatment apparatus 16 and a patient 20 can be facilitated by providing a number of markers 30-40 attached to the surface of the main body of the treatment apparatus, the gantry 24, the collimator 26 and the couch 18 respectively. By providing the stereoscopic camera system 10 with an appropriate light source and making the markers reflective, it becomes possible to identify the portions of the images corresponding to the markers 30-40 by performing a thresholding operation. This enables the portions of images corresponding to the markers 30-40 to be rapidly identified. The processing of images to identify portions of images corresponding to the markers 30-40 can additionally be facilitated by using the expected or monitored positions of the treatment apparatus 16 and mechanical couch 18 to identify the expected portions of an image where markers 30-40 are expected to be viewed.

The positioning and format of the markers 30-40 need to be chosen to account for different portions of the treatment apparatus 16 and couch 18 being obscured at different times depending on their relative locations and the position of the patient 20 on the mechanical couch 18. Additionally where reflective markers are utilized, the relative positioning of the stereoscopic camera 10 and the markers 30-40 needs to be taken into account.

One suitable arrangement of markers 30-40 is to place the markers 30-40 as follows.

In order to track the rotation of the gantry 24 relative to the main body of the treatment apparatus, two markers 30,31 (marker 31 is not visible in FIG. 1, but is located on the remote side of the gantry 24, in a correspondingly symmetrical position to marker 30) may be placed on the gantry head and two markers 32,33 may be placed on the body portion of the treatment apparatus adjacent the main body 22 of the apparatus 16, the markers 30-33 thereby identifying the four corners of a square or rectangle. This arrangement of four markers 30-33 ensures that at all times 3 or more markers are in the field of view of a stereoscopic camera system 10 placed opposite the treatment apparatus 16 such as is illustrated in FIG. 1. In the arrangement such as is illustrated in FIG. 1 where the camera planes of the cameras of the stereoscopic camera system 10 are substantially aligned with the plane of rotation of the gantry 24, the markers 30-33 used to track the rotation of the gantry 24 can be portions of reflective material stuck on to the surface of the treatment apparatus viewed by the camera system 10. The alignment of camera planes of the cameras of the stereoscopic camera system 10 and the plane of rotation of the gantry 24 simplifies tracking as rotation of the gantry 24 should only cause the apparent positions of the markers 30-33 to vary and not change the apparent size or shape of the markers 30-33.

In order to maximize the accuracy with which the rotation of the gantry 24 can be monitored, it is preferred that the shape and appearance of the markers 30-33 should be such that the centres of the markers 30-33 as they appear in images obtained by the stereoscopic camera system 10 can be easily determined. In this embodiment this is achieved by utilizing circular markers and processing image data to identify the centres of the imaged markers 30-33.

In the case of the collimator 26, where the camera planes of the cameras of the stereoscopic camera system 10 are substantially aligned with the plane of rotation of the gantry 24, the collimator 26 will be arranged to rotate in a plane which is at right angles to the camera planes of the cameras of the stereoscopic camera system 10. This will mean that as the collimator 26 rotates different portions of the collimator 26 will be presented in the field of view of the stereoscopic camera system 10. Because of this in order to track the rotation of the collimator 26, it is preferred that the markers 34-38 present on the collimator 26 should be grouped in distinctive patterns so that the presence or absence of particular patterns or markers 34-38 can enable the rotational position of the collimator 26 to be inferred. Thus for example the markers 34-38 might be arranged in four groups spaced equally around the circumference of the collimator 26 in slightly different patterns e.g. one group might consist of a single marker 38 (not shown in FIG. 1 but visible in FIGS. 5A and 5B), one group might consist of two markers 36, 37 immediately adjacent each other, another group might consist of two markers 34, 35 spaced apart and a third group might consist of three markers (not shown in the Figures) on the opposite side of the collimator 26 to one of the other groups. In the illustrated embodiment, this would be the side of the collimator 26 opposite and remote from the pair of spaced apart markers 34, 35. In this way whenever two groups of markers were visible, the identity of the groups could be identified and the rotational position of the collimator inferred from the apparent position of the visible markers and the identity of the visible groups.

As with the markers 30-33 for tracking the rotation of the gantry 24 it is preferable that the shape an appearance of the markers 34-38 should be such that the centres of the markers 34-38 for tracking the rotation of the collimator 26 should also be easily determined. As the rotation of the collimator 26 varies the location, distance and orientation of markers 34-38 on the collimator 26 relative to the camera planes of the cameras of the stereoscopic camera system 10, as well as the shape and appearance of the markers 34-38 will vary as the collimator 26 is rotated. This variance can be reduced by utilizing spherical markers as only the apparent size and not the apparent shape of the markers will vary, hence simplifying the identification of the locations of centre of the markers.

The location and orientation of the mechanical couch 18 can be tracked using a pair of markers 39,40 located near or adjacent the portion of the patient 20 which is imaged by the stereoscopic camera system 10. In a typical treatment system normally there is capacity for attaching additional equipment to a mechanical couch 18 for treatment purposes and suitable tracking markers 39,40 can be attached in the same way. Suitable locations can include being placed on the surface of the bed of the mechanical couch 18 adjacent where the head of a patient will lie 40 or alternatively markers may be attached to the edge 39 of the bed of the couch in the vicinity of the portion of the patient 20 being imaged.

Again as in the case of markers for tracking the rotation of the collimator 26, it is preferable to utilize spherical markers for tracking the location and orientation of the mechanical couch 18 as the relative orientation and distance of the markers 39,40 and the camera plane of the cameras in the stereoscopic camera system 10 will vary as the location and orientation of the couch 18 is varied.

Monitoring the location of a patient 20 and the orientation and movement of a treatment apparatus 16 and a mechanical couch 18 utilizing the same stereoscopic camera 10 gives rise to a number of advantages.

Firstly monitoring both the position of the patient 20 and the treatment apparatus 16 during treatment enables the application of radiation to be compared in real time with a treatment plan. The timing and movement of a treatment apparatus 16 in accordance with a treatment plan is usually determined relative to the iso-centre of the treatment apparatus (i.e. a fixed point irradiated by the treatment apparatus 16 and about which the treatment apparatus 16 is considered to rotate. In theory the mechanical couch 18 causes a tumour in the patient 20 to be positioned at that iso-centre and the treatment causes the tumour to be irradiated from different angles in the course of treatment. It is, however, ultimately the irradiation of the tumour rather than irradiation of the iso-centre which is ultimately important and by monitoring the surface of the patient 20 and the movement of the treatment apparatus 16 it is possible for the actual irradiation of a tumour site to be monitored.

In addition to being able to confirm the actual history of irradiation of a tumour site in terms of a position relative to a detected surface of a patient 20, the described system also facilitates improved quality control and confirmation of the accuracy of the stereoscopic camera system 10. Thus for example, by arranging for markers 39,40 to be attached to a mechanical couch 18 when calibrating the system, it is possible to move the mechanical couch 18 and hence the attached markers 39,40 predefined distances in predefined directions. This enables the calibration of the stereoscopic camera system 10 to be performed across a wide volume which is liable to subsequently contain the surface of a patient 20 being monitored and hence the stereoscopic camera system 10 can be calibrated accurately throughout this volume of interest. When calibrating the stereoscopic camera 10 it is also desirable for the co-ordinate system of the stereoscopic camera 10 to match that used by the treatment plan for the treatment apparatus 16 and mechanical couch 18. One way this can be done is through monitoring a calibration model of known dimensions on the surface of the mechanical couch 18 and then moving the couch laterally, horizontally and vertically to determine axes corresponding to the axes of couch motion. Monitoring the movement of the treatment apparatus 16 itself provides further confirmation of the co-ordinate system the treatment apparatus is arranged to operate. In contrast to the mechanical couch 18, a treatment apparatus 16 is normally only arranged to rotate about a fixed point. This means that monitoring the position of markers attached to the treatment apparatus should identify a plane of rotation containing the markers 30-33 which in turn should correspond with the co-ordinate system for couch movement. This additional information can again be utilized to calibrate the co-ordinate system for the stereoscopic cameras 10 and any change in the measured plane of movement of the markers can be detected and investigated. Again as with the monitoring of motion of the mechanical couch 18 such calibration and confirmation can be determined for a relatively large volume and hence the reliability of calibration can be increased.

Figure 2:
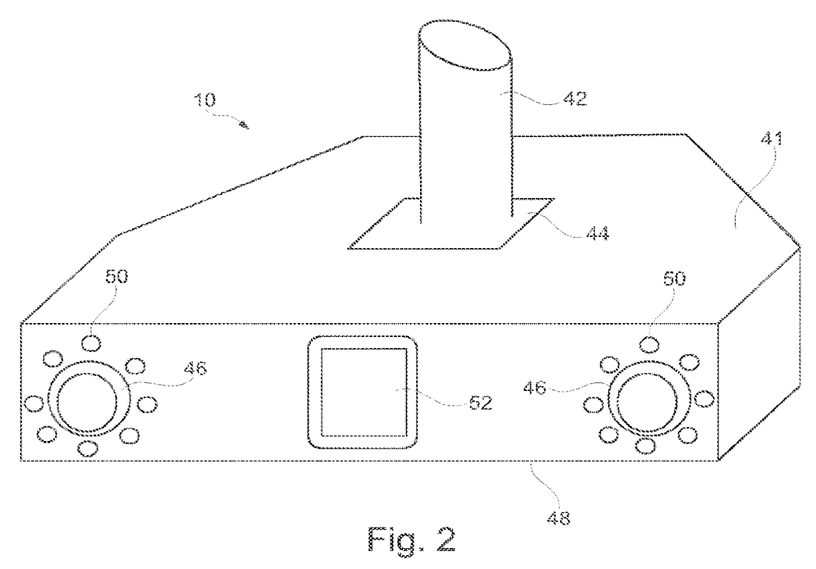
FIG. 2 is a front perspective view of the camera system of the patient monitor of FIG. 1.

FIG. 2 is a front perspective view of the camera system 10 of the patient monitor of FIG. 1.

In this embodiment the camera system 10 comprises a housing 41 which is connected to a bracket 42 via a hinge 44. The bracket 42 enables the camera system 10 to be attached in a fixed location to the ceiling of a treatment room whilst the hinge 44 permits the orientation of the camera system 10 to be orientated relative to the bracket 42 so that the camera system 10 is arranged to view a patient 20 on a mechanical couch 18.

A pair of lenses 46 is mounted at either end of the front surface 48 of the housing 41. These lenses 46 are positioned in front of image detectors such as CMOS active pixel sensors or charge coupled devices (not shown) contained within the housing 41. The image detectors are arranged behind the lenses 46 so as to capture images of a patient 20 via the lenses 46.

A set of LED lights 50 is positioned around the outside of the circumference of each of the lenses 46. The LED lights 50 are orientated to illuminate the field of view of the camera system 10 and in particular the retro-reflective markers 30-40 attached to the treatment apparatus 16 and the mechanical couch 18.

A speckle projector 52 is provided in the middle of the front surface 48 of the housing 41 between the two lenses 46. The speckle projector 52 is arranged to illuminate a patient 20 with a non-repeating speckled pattern of infrared light so that when images of a patient 20 are captured by the two image detectors corresponding portions of captured images can be distinguished. To that end the speckle projector comprises a light source such as a LED and a film with a random speckle pattern printed on the film. In use light from the light source is projected via the film and as a result a pattern consisting of light and dark areas is projected onto the surface of a patient 20. When images of the projected speckle pattern are captured by the camera system 10 the images can then be processed to determine the positions of a set of points on the surface of the patient and hence the positioning of the patient can be monitored.

Figure 3:
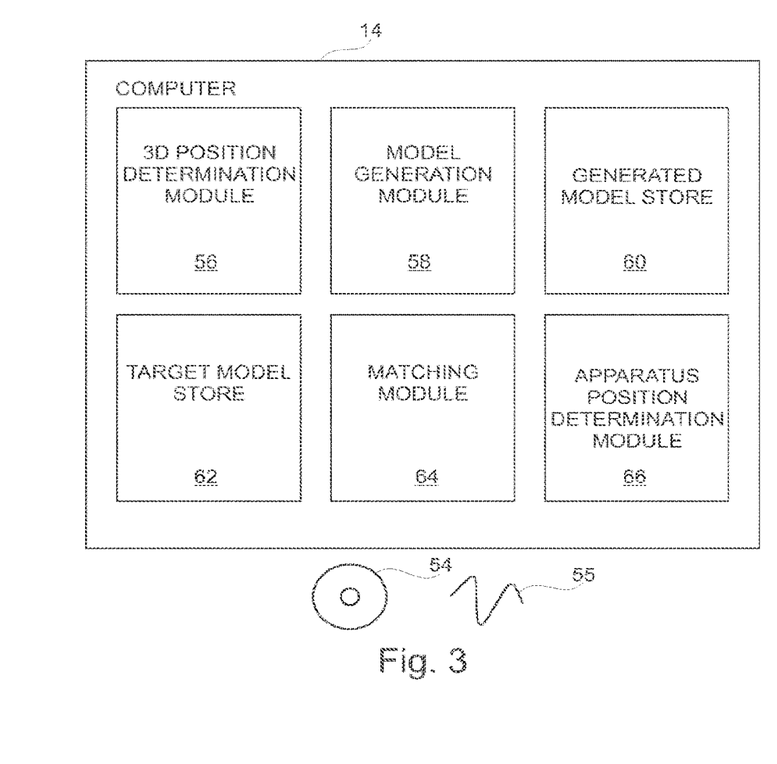
FIG. 3 is a schematic block diagram of the computer system of the patient monitor of FIG. 1.

FIG. 3 is a schematic block diagram of the computer 14 of the patient monitor of FIG. 1.

In order for the computer 14 to process images received from the stereoscopic cameras 10, the computer 14 is configured by software either provided on a disk 54 or by receiving an electrical signal 55 via a communications network into a number of functional modules 56-66. It will be appreciated that the functional modules 56-66 illustrated in FIG. 3 are purely notional in order to assist with the understanding of the working of the claimed invention and may not in certain embodiments directly correspond with blocks of code in the source code for the software. In other embodiments the functions performed by the illustrated functional modules 56-66 may be divided between different modules or may be performed by the re-use of the same modules for different functions.

In this embodiment, the functional modules 56-66 comprise: a 3D position determination module 56 for processing images received from the stereoscopic cameras 10, a model generation module 58 for processing data generated by the 30 position determination module 56 and converting the data into a 30 wire mesh model of an imaged computer surface; a generated model store 60 for storing a 30 wire mesh model of an imaged surface; a target model store 62 for storing a previously generated 30 wire mesh model; a matching module 64 for determining rotations and translations required to match a generated model with a target model; and an apparatus position determination module 66.

In use, as images are obtained by the stereoscopic cameras 10, these images are processed by the 30 position determination module 56. This processing enables the 30 position determination module to identify 30 positions of corresponding points in pairs of images on the surface of a patient 20. This is achieved by the 30 position determination module 56 identifying corresponding points in pairs of images obtained by the stereoscopic camera system 10 and then determining 30 positions for those points based on the relative positions of corresponding points in obtained pairs of images and stored data identifying the relative positions of cameras obtaining the images.

Typically the identification of corresponding points is based on analysis of image patches of around 16×16 pixels. In order to assist with identifying and matching corresponding patches as has been described the stereoscopic camera system 10 includes a speckle projector 52 arranged to project a random or quasi random speckle pattern onto the patient 20 being imaged so that different portions of the surface of the patient 20 can be more easily distinguished. The size of the speckle pattern is selected so that different patterns will be apparent in different image patches.

The position data generated by the 30 position determination module 56 is then passed to the model generation module 58 which processes the position data to generate a 30 wire mesh model of the surface of a patient 20 imaged by the stereoscopic cameras 10. In this embodiment the 30 model comprises a triangulated wire mesh model where the vertices of the model correspond to the 30 positions determined by the 30 position determination module 56. When such a model has been determined it is stored in the generated model store 60.

When a wire mesh model of the surface of a patient 20 has been stored, the matching module 64 is then invoked to determine a matching translation and rotation between the generated model based on the current images being obtained by the stereoscopic cameras 10 and a previously generated model surface of the patient stored in the target model store 62. The determined translation and rotation can then be sent as instructions to the mechanical couch 18 to cause the couch to position the patient 20 in the same position relative to the treatment apparatus 16 as they were when they were previously treated.

Subsequently, the stereoscopic cameras 10 can continue to monitor the patient 20 and any variation in position can be identified by generating further model surfaces and comparing those generated surfaces with the target model stored in the target model store 62. If it is determined that a patient has moved out of position, the treatment apparatus 16 can be halted and the patient 20 repositioned, thereby avoiding irradiating the wrong parts of the patient 20.

In addition to monitoring the positioning of the patient 20, the computer 14 also includes an apparatus position determination module 66. As will be described, the apparatus position determination module 66 is arranged to process images captured by the stereoscopic camera system 10 and identify the portions of the images corresponding to the markers 30-40 attached to the treatment apparatus 16 and the mechanical couch 18. The apparatus position determination module 66 is then arranged to utilize the identified portions of the images to determine the positioning of the treatment apparatus 16 and the mechanical couch 18. This enables the positioning of treatment apparatus 16 and the mechanical couch 18 to be monitored in real time simultaneously with the monitoring of the positioning of the patient 20. The positioning of the treatment apparatus 16 and the mechanical couch 18 can then be compared with a predefined treatment plan to confirm that the correct portions of the patient are being irradiated.

Additionally determining the current position and orientation of the patient 20, treatment apparatus 16 and the mechanical couch 18 enables the computer system 14 to determine if a collision is likely to occur and if necessary provide a warning or halt treatment before such a collision happens.

Figure 4:
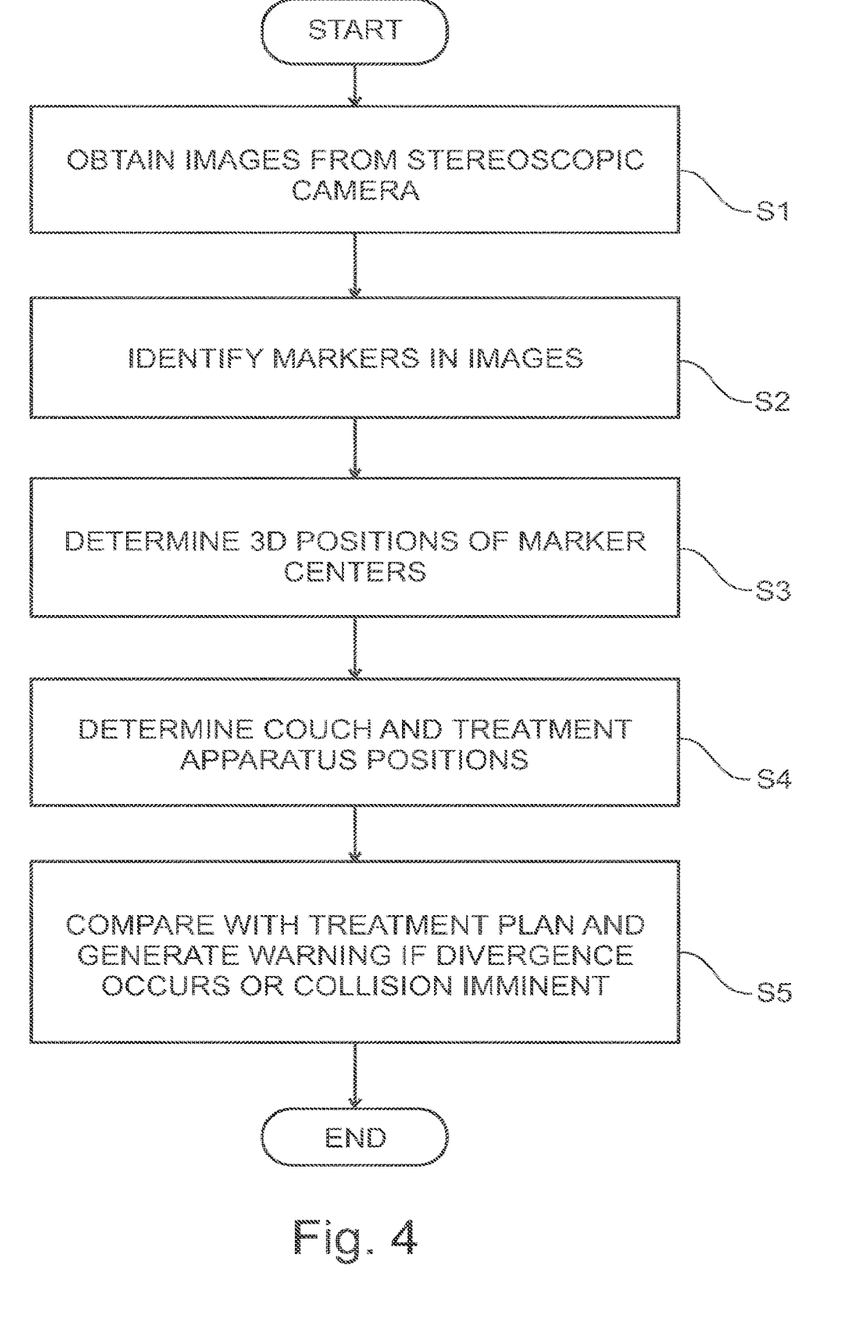
FIG. 4 is a flow diagram of the processing undertaken by the apparatus position determination module in the computer system of the patient monitor of FIG. 1.

The processing of the apparatus position determination module 66 will now be described with reference to FIG. 4 which is a flow diagram of the processing undertaken by the apparatus position determination module 66 and FIGS. 5A and 5B.

In this embodiment the apparatus position determination module 66 operates in parallel with the 30 position determination module S6 and the model generation module 58 to determine the current position and orientation of the treatment apparatus 16 and mechanical couch 18 while the 30 position determination module 56 and the model generation module 58 generates a wire mesh model of the surface of a patient 20 being monitored.

The apparatus position determination module 66 is invoked (s1) when it receives a pair of images from the stereoscopic camera system 10. These images will comprise images obtained from the image detectors behind the lenses 46 of the stereoscopic camera system 10 and hence will be images of the area of view of the stereoscopic camera system 10 obtained from slightly different viewpoints.

Figure 5A:
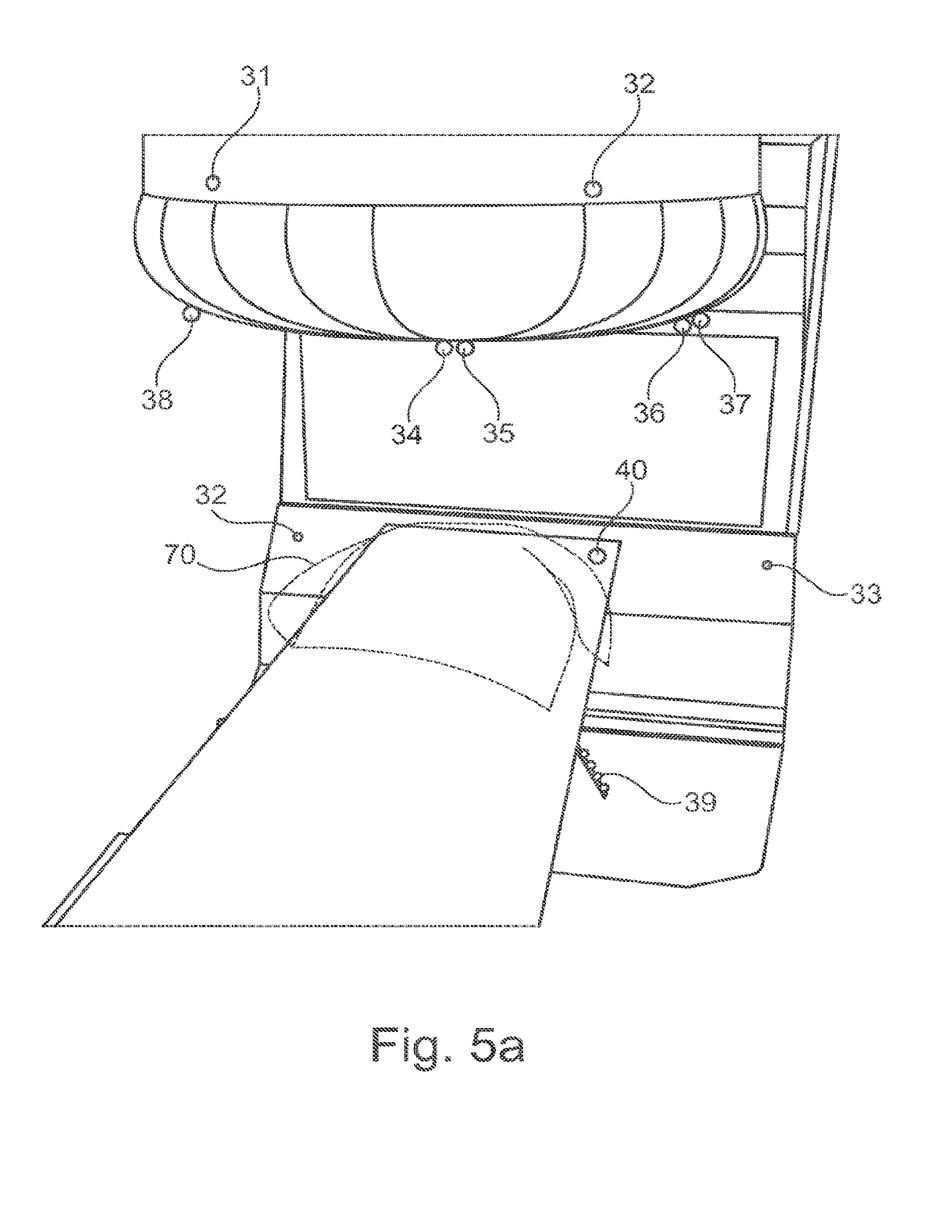
FIGS. 5A and 5B are illustrative representations of images captured by the camera system of the patient monitor of FIG. 1.
Figure 5B:
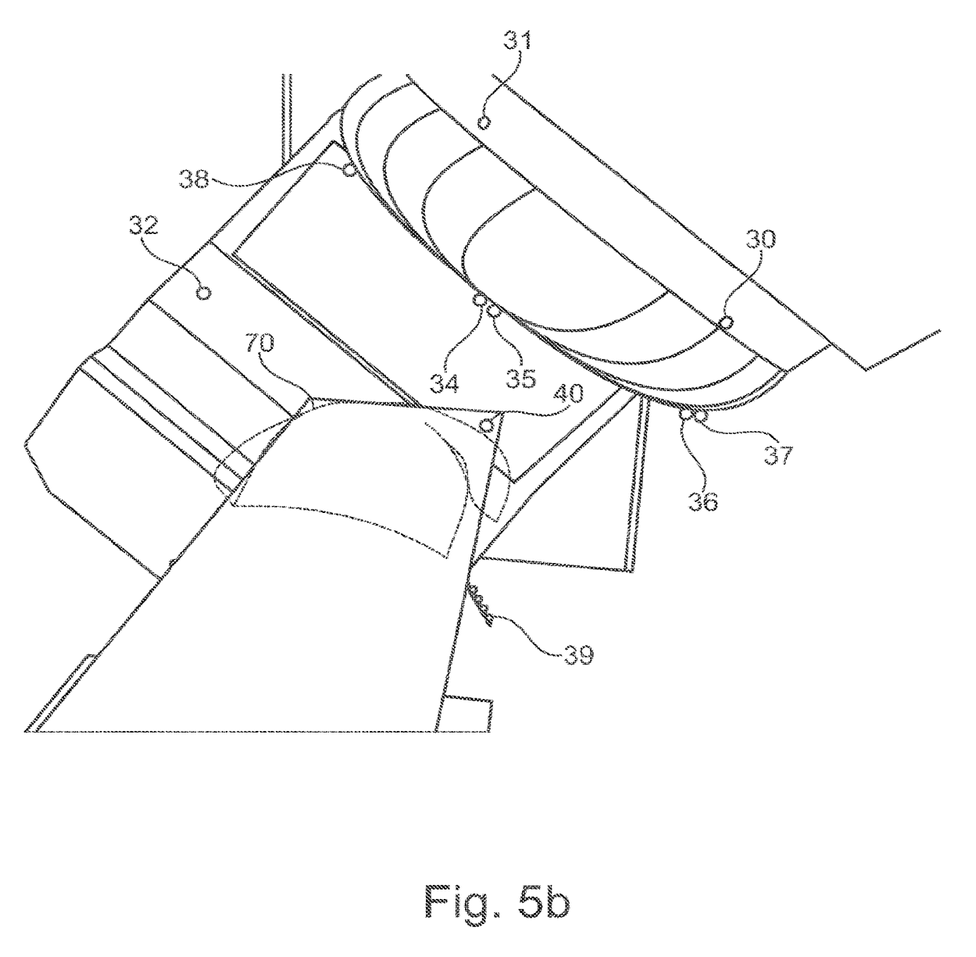

Examples of images of the mechanical couch 18 and treatment apparatus 16 at different points in time in different orientations are illustrated in FIGS. 5A and 5B. More specifically, FIGS. 5A and 5B illustrate views of the mechanical couch 18 and treatment apparatus 16 where the gantry 24 of the treatment apparatus has been rotated relative to the main body 22 in FIG. 5B relative to the position in FIG. 5A. In FIGS. 5A and 5B, in addition to the treatment apparatus 16 and the mechanical couch 18, a surface 70 corresponding to a portion of a patient 20 being monitored is illustrated in broken outline.

As can be seen in FIGS. 5A and 5B in the images representations of the markers 30-40 can be seen and the positions and locations of the markers 30-40 are indicative of the location and orientation of the treatment apparatus 16 and the mechanical couch 18. Also as will be apparent viewing FIGS. 5A and 5B specific markers are obscured from view depending on the location and orientation of the treatment apparatus 16 and the mechanical couch 18 and also the portion of the image occupied by the patient 20 being monitored.

Having received images from the stereoscopic camera 10, the apparatus position determination module 66 then (s2) proceeds to identify the representations of the markers 30-40 in the obtained images.

In this embodiment this is achieved in a two-step process. Initially the apparatus position determination module 66 performs a thresholding operation on the images to identify portions of the images which are particularly bright. These portions of the images should correspond to the locations of the markers 30-40 as, as has been explained, the markers are arranged to be retro-reflective and illuminated by the LED lights 50 located around the circumference of the lenses 46 of the camera system 10.

Having performed a thresholding operation, the candidate portions of image are then in this embodiment checked to see if the identified bright portions of the image are approximately circular and hence correspond to the circular or spherical markers 30-40 on the treatment apparatus 16 and mechanical couch 18. A suitable determination can be made by calculating the ratio of the numbers of pixels identified in an area of an image having a brightness value above a particular threshold, in comparison with the numbers of pixels at the perimeter of that area.

Additionally, the apparatus position determination module 66 can also check whether the identified bright areas of image are in a position in the image where the markers would be expected to be. Where the apparatus position determination module 66 is processing a sequence of images this can be achieved both by determining whether the identified bright areas are in the vicinity of areas previously identified as being markers in an earlier image. Further confirmation can be achieved by the apparatus position determination module 66 modelling the expected appearance of the treatment apparatus 16 and mechanical couch 18 based on data identifying the treatment plan and checking whether the identified bright areas appear where expected.

Having identified the brightest areas in the image and filtered candidates to exclude portions of the image which do not correspond in shape or the expected locations of the markers 30-40, the apparatus position determination module 66 then (s3) proceeds to use the identified areas to calculate the 3D positions of the centres of the imaged markers 30-40.

The 3D positions of the centres of the imaged markers 30-40 can be determined by determining the co-ordinates of the centre of a portion of an image corresponding to a marker and then comparing the location of the marker between the pair of images taken by the two cameras of the stereoscopic camera system 10. In order to identify the centre of the representation of a marker, a weighted average of the co-ordinates having a brightness above a threshold can be determined.

These co-ordinates can then be processed into 3D co-ordinates based on the relative locations of corresponding points in the two images and the location of the camera planes of the two image detectors contained within the stereoscopic camera system 10.

In some embodiments, improved accuracy of the determination of the 2D co-ordinates of a point corresponding to a marker can be determined by utilizing the original grayscale image data for a section of an image and determining an average weighted co-ordinate value for the section of an image corresponding to a marker where the average weighted co-ordinate value is weighted by greyscale level. This is because in general retro-reflective markers will appear as bright white in an obtained image but at the periphery pixels may appear to be grey where only part of a pixel corresponds to the surface of a marker 30-40.

Having processed a pair of images to determine the 3D location of imaged markers 30-40, the 3D locations are then (s4) utilized to determine the position and orientation of the treatment apparatus 16 and mechanical couch 18. In making such a determination, the apparatus position determination module 66 may determine the relative location and orientations of the treatment apparatus 16 and mechanical couch 18 based on the relative positions of the identified markers 30-40. Thus for example as has been described above the locations of the markers 30-33 attached to the treatment apparatus 16 can be utilized to determine the rotational orientation of the gantry 24 relative to the main body 22 of the treatment apparatus 22. Similarly, the rotational position of the collimator 24 can be inferred from the positions and grouping of the markers 34-38 attached to the collimator 24 etc.

Having determined the position and orientation of treatment apparatus 16 and mechanical couch 18 based on the images obtained by the stereoscopic camera 10, the apparatus position determination module 66 can then (s5) compare the measured position and orientation with the position and orientation the treatment apparatus 16 and mechanical couch 18 would be expected to be in based on a treatment plan. More specifically the apparatus position determination module 66 can compare the expected positions of the treatment apparatus 16 and mechanical couch 18 relative to both the iso-centre of the apparatus and also with the estimated location of a tumour being treated based on the surface model of the surface of the patient being treated. Thus in this way the apparatus position determination module 66 can provide a real time measurement of a deviation from the treatment plan and provide a warning if the deviation is greater than a threshold amount.

Finally in addition to monitoring and detecting any deviation from a treatment plan the apparatus position determination module 66 can also utilize the measured orientation and location for the treatment apparatus 16 and mechanical couch 18 and the measurement of the surface of a patient 20 to determine whether any portion of the treatment apparatus 16 is dangerously close to colliding with either the patient 20 or the mechanical couch 18 and provide a warning or halt treatment in the event that any such collision is liable to occur.

Although in the embodiment described in detail above, portions of images captured by a stereoscopic camera system 10 which are not utilized to generate a model of the surface of a patient 20 is described as being utilized to monitor the orientation and positioning of a treatment apparatus 16 and a mechanical couch 18, it will be appreciated that in other embodiments other additional forms of monitoring could be undertaken.

In particular, when undertaking radiotherapy, particularly in the case of brain tumours or the like, frequently patients are required to wear a rigid face mask to hold their head in a fixed position during treatment. If the wrong face mask is worn, this can be very dangerous as the face masks are formed to be specific to individual users and use of the wrong mask may not secure a patient properly leading to the possibility of movement and hence irradiating the wrong part of the patient 20. This is a particular problem in the case of brain tumours where damage to adjacent areas of the brain can cause very significant problems. The applicants have appreciated that, when utilizing a stereoscopic camera system 10 for patient positioning, portions of the periphery of an image corresponding to part of a face mask could be utilized to confirm that the correct face mask was being used. In such a system instead of using such a section of the image for patient monitoring, the face mask could be marked in a distinctive way, for example with a bar code or the like and when imaging a patient the presence of the bar code could be detected and checked to confirm that the correct face mask was being used.

Although in the above system a monitoring system based on the projection of a speckle pattern onto the surface of a patient and the tracking of markers 30-40 attached to a treatment apparatus 16 and mechanical couch 18 has been described, it will be appreciated that other monitoring systems could be utilized. Thus for example rather than generating a model of the surface of a patient using the projection of a speckle pattern other approaches such as the use of structured light could be used. Also rather than monitoring the location of markers, in some embodiments models of the surface of the treatment apparatus 16 and mechanical couch could be generated and used to monitor the positioning of a patient relative to the treatment apparatus. Monitoring the movement of the treatment apparatus 16 and mechanical couch 18 using markers 30-40 is, however, preferable as this can be achieved by undertaking limited processing and therefore can be undertaken simultaneously with the modeling of the surface of a patient 20 in real-time without excessive resource demands. Additionally the use of markers 30-40 for determining apparatus location is more reliable than trying to infer apparatus orientation based on generating a model of an apparatus surface as much of an apparatus will be self similar and hence the apparatus would need to be monitored over a wide field of view in order for its position and orientation to be established.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier can be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means. When a program is embodied in a signal which may be conveyed directly by a cable or other device or means, the carrier may be constituted by such cable or other device or means. Alternatively, the carrier may be an integrated circuit in which the program is embedded, the integrated circuit being adapted for performing, or for use in the performance of, the relevant processes.

The invention claimed is:

1. A radiotherapy treatment system comprising:
   a movable radiotherapy treatment apparatus configured to focus a beam of a radiation source on a treatment target of a patient;
   a movable couch configured to hold the patient, wherein the movable couch is configured for positioning the patient to align the treatment target with the beam, wherein predefined positions of the patient and the movable radiotherapy treatment apparatus are operated according to a predefined treatment plan during a course of radiotherapy treatment;
   a camera system configured to obtain images of the patient; and
   a control system configured to:
   receive the images from the camera system;
   obtain at least one of a position of the movable couch and a position of the movable radiotherapy treatment apparatus during the course of radiotherapy treatment;
   generate, based on the images, a patient surface model of at least a part of the patient containing the treatment target;
   compare the patient surface model with at least one of the predefined positions; and
   track the patient surface model in relation to the at least one obtained position.

2. The radiotherapy treatment system of claim 1, wherein the movable radiotherapy treatment apparatus or the movable couch comprises a plurality of markers, and wherein the control system is configured to obtain the at least one position based on the plurality of markers.

3. The radiotherapy treatment system of claim 2, wherein obtaining the at least one position comprises applying a thresholding operation based on light intensity of the plurality of markers.

4. The radiotherapy treatment system of claim 1, wherein the control system is configured to obtain the position of the movable couch and the position of the movable radiotherapy treatment apparatus during the course of radiotherapy treatment, wherein the movable radiotherapy treatment apparatus and the movable couch comprise a plurality of markers, and wherein the control system is configured to obtain the positions based on the plurality of markers.

5. The radiotherapy treatment system of claim 4, wherein obtaining the positions comprises applying a thresholding operation based on light intensity of the plurality of markers.

6. The radiotherapy treatment system of claim 1, wherein the patient surface model is a wire mesh model.

7. The radiotherapy treatment system of claim 1, wherein the control system is configured to align the patient surface model with a computer model of the movable radiotherapy treatment apparatus and the movable couch.

8. The radiotherapy treatment system of claim 1, wherein the control system is configured to:
   determine, based on the tracking of the patient surface model, whether the patient will collide with the movable radiotherapy treatment apparatus; and
   in accordance with a determination that the patient will collide with the movable radiotherapy treatment apparatus, generate and output a warning.

9. The radiotherapy treatment system of claim 1, wherein in accordance with a determination that the patient will collide with the movable radiotherapy treatment apparatus, the control system is further configured to stop movement of the movable couch or the movable radiotherapy treatment apparatus.

10. The radiotherapy treatment system of claim 1, wherein the control system is configured to operate in real-time.

11. The radiotherapy treatment system of claim 1, wherein the control system is configured to obtain the at least one position by generating and monitoring at least one of a model of a surface of the movable radiotherapy treatment apparatus and a model of a surface of the movable couch.

* * * * *